United States Patent
Clucas

(10) Patent No.: US 7,635,807 B1
(45) Date of Patent: Dec. 22, 2009

(54) INBRED CORN LINE G07-NPID4480

(75) Inventor: Christopher Clucas, Rochelle, IL (US)

(73) Assignee: Syngenta Participations AG, Basel (CH)

( * ) Notice: Subject to any disclaimer, the term of this patent is extended or adjusted under 35 U.S.C. 154(b) by 3 days.

(21) Appl. No.: 11/983,773

(22) Filed: Nov. 9, 2007

(51) Int. Cl.
- *A01H 5/00* (2006.01)
- *A01H 5/10* (2006.01)
- *A01H 1/02* (2006.01)
- *C12N 5/04* (2006.01)

(52) U.S. Cl. .................... 800/320.1; 800/275; 800/284; 800/300.1; 800/303; 435/412; 435/424

(58) Field of Classification Search ........................ None
See application file for complete search history.

(56) References Cited

U.S. PATENT DOCUMENTS 7,462,765 B1 * 12/2008 Baltenberger ............ 800/320.1

OTHER PUBLICATIONS

U.S. Appl. No. 60/904,643, filed Mar. 1, 2007.
U.S. Appl. No. 12/072,734, filed Feb. 28, 2008.
U.S. Appl. No. 12/393,298, filed Feb. 29, 2009.
PVP 200800045 filed Dec. 4, 2007.
PVP 200900024 filed Oct. 31, 2008.

* cited by examiner

*Primary Examiner*—David T Fox
(74) *Attorney, Agent, or Firm*—Dana Rewoldt

(57) ABSTRACT

Basically, this invention provides for an inbred corn line designated G07-NPID4480, methods for producing a corn plant by crossing plants of the inbred line G07-NPID4480 with plants of another corn plant. The invention relates to the various parts of inbred G07-NPID4480 including culturable cells. This invention also relates to methods for introducing transgenic transgenes into inbred corn line G07-NPID4480 and plants produced by said methods.

19 Claims, No Drawings

INBRED CORN LINE G07-NPID4480

FIELD OF THE INVENTION

This invention is in the field of corn breeding, specifically relating to an inbred corn line designated G07-NPID4480. This invention also is in the field of hybrid maize production employing the present inbred.

BACKGROUND OF THE INVENTION

The original maize plant was indigenous to the Western Hemisphere. The plants were weed like and only through the efforts of early breeders were cultivated crop species developed. The crop cultivated by early breeders, like the crop today, could be wind pollinated. The physical traits of maize are such that wind pollination results in self-pollination or cross-pollination between plants. Each maize plant has a separate male and female flower that contributes to pollination, the tassel and ear, respectively. Natural pollination occurs when wind transfers pollen from tassel to the silks on the corn ears. This type of pollination has contributed to the wide variation of maize varieties present in the Western Hemisphere.

The development of a planned breeding program for maize only occurred in the last century. A large part of the development of the maize product into a profitable agricultural crop was due to the work done by land grant colleges. Originally, maize was an open pollinated variety having heterogeneous genotypes. The maize farmer selected uniform ears from the yield of these genotypes and preserved them for planting the next season. The result was a field of maize plants that were segregating for a variety of traits. This type of maize selection led to; at most, incremental increases in seed yield.

Large increases in seed yield were due to the work done by land grant colleges that resulted in the development of numerous hybrid corn varieties in planned breeding programs. Hybrids were developed from inbreds which were developed by selecting corn lines and selfing these lines for several generations to develop homozygous pure inbred lines. One selected inbred line was emasculated and another selected inbred line pollinated the emasculated inbred to produce hybrid seed F1 on the emasculated inbred line. Emasculation of the inbred usually is done by detasseling the seed parent; however, emasculation can be done in a number of ways. For example an inbred could have a male sterility factor which would eliminate the need to detassel the inbred.

In the early seventies the hybrid corn industry attempted to introduce CMS (cytoplasmic male sterility) into a number of inbred lines. Unfortunately, the CMS inbreds also introduced some very poor agronomic performance traits into the hybrid seed which caused farmers concern causing the maize industry to shy away from CMS material for a couple of decades thereafter.

However, in the last 10-15 years a number of different male sterility systems for maize have been successfully deployed. The most traditionally of these male sterility and/or CMS systems for maize parallel the CMS type systems that have been routinely used in hybrid production in sunflower.

In the standard CMS system there are three different maize lines required to make the hybrid. First, there is a cytoplasmic male-sterile line usually carrying the CMS or some other form of male sterility. This line will be the seed producing parent line. Second, there must be a fertile inbred line that is the same or isogenic with the seed producing inbred parent but lacking the trait of male sterility. This is a maintainer line needed to make new inbred seed of the seed producing male sterile parent. Third there is a different inbred which is fertile, has normal cytoplasm and carries a fertility restoring gene. This line is called the restorer line in the CMS system. The CMS cytoplasm is inherited from the maternal parent (or the seed producing plant); therefore for the hybrid seed produced on such plant to be fertile the pollen used to fertilize this plant must carry the restorer gene. The positive aspect of this is that it allows hybrid seed to be produced without the need for detasseling the seed parent. However, this system does require breeding of all three types of lines: 1) male sterile—to carry the CMS; 2) the maintainer line; and, 3) the line carrying the fertility restorer gene.

In some instances, sterile hybrids are produced and the pollen necessary for the formation of grain on these hybrids is supplied by interplanting of fertile inbreds in the field with the sterile hybrids.

Whether the seed producing plant is emasculated due to detasseling or CMS or transgenes, the seed produced by crossing two inbreds in this manner is hybrid seed. This hybrid seed is F1 hybrid seed. The grain produced by a plant grown from a F1 hybrid seed is referred to as F2 or grain. Although, all F1 seed and plants, produced by this hybrid seed production system using the same two inbreds should be substantially the same, all F2 grain produced from the F1 plant will be segregating maize material.

The hybrid seed production produces hybrid seed which is heterozygous. The heterozygosis results in hybrid plants, which are robust and vigorous plants. Inbreds on the other hand are mostly homozygous. This homozygosity renders the inbred lines less vigorous. Inbred seed can be difficult to produce since the inbreeding process in corn lines decreases the vigor. However, when two inbred lines are crossed, the hybrid plant evidences greatly increased vigor and seed yield compared to open pollinated, segregating maize plants. An important consequence of the homozygosity and the homogeneity of the inbred maize lines is that all hybrid seed produced from any cross of two such elite lines will be the same hybrid seed and make the same hybrid plant. Thus the use of inbreds makes hybrid seed which can be reproduced readily.

The ultimate objective of the commercial maize seed companies is to produce high yielding, agronomically sound plants that perform well in certain regions or areas of the Corn Belt. To produce these types of hybrids, the companies must develop inbreds, which carry needed traits into the hybrid combination. Hybrids are not often uniformly adapted for the entire Corn Belt, but most often are specifically adapted for regions of the Corn Belt. Northern regions of the Corn Belt require shorter season hybrids than do southern regions of the Corn Belt. Hybrids that grow well in Colorado and Nebraska soils may not flourish in richer Illinois and Iowa soils. Thus, a variety of major agronomic traits is important in hybrid combination for the various Corn Belt regions, and has an impact on hybrid performance.

Inbred line development and hybrid testing have been emphasized in the past half-century in commercial maize production as a means to increase hybrid performance. Inbred development is usually done by pedigree selection. Pedigree selection can be selection in an F2 population produced from a planned cross of two genotypes (often elite inbred lines), or selection of progeny of synthetic varieties, open pollinated, composite, or backcrossed populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include: yield potential in hybrid combination; dry down; maturity; grain moisture at harvest; greensnap; resistance to root lodging; resistance to stalk lodging; grain quality; disease and insect resistance; ear and plant height. Additionally, hybrid performance will differ in different soil types such as low levels of organic matter, clay, sand, black, high pH, low pH; or in different environments such as wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. In addition, most traits in the corn genome are regrettably not single dominant genes but are multi-genetic with additive gene action not dominant gene action. Thus, the general procedure of producing a non segregating F1 generation and self pollinating to produce a F2 generation that segregates for traits and selecting progeny with the visual traits desired does not easily lead to an useful inbred. Great care and breeder expertise must be used in selection of breeding material to continue to increase yield and the agronomics of inbreds and resultant commercial hybrids.

Certain regions of the Corn Belt have specific difficulties that other regions may not have. Thus the hybrids developed from the inbreds have to have traits that overcome or at least minimize these regional growing problems. Examples of these problems include in the eastern Corn Belt Gray Leaf Spot, in the north cool temperatures during seedling emergence, in the Nebraska region CLN (Corn Lethal Necrosis) and in the west soil that has excessively high pH levels. The industry often targets inbreds that address these issues specifically forming niche products. However, the aim of most large seed producers is to provide a number of traits to each inbred so that the corresponding hybrid can be useful in broader regions of the Corn Belt. The new biotechnology techniques such as Microsatellites, RFLPs, RAPDs and the like have provided breeders with additional tools to accomplish these goals.

SUMMARY OF THE INVENTION

The present invention relates to an inbred corn line G07-NPID4480. Specifically, this invention relates to plants and seeds of this line. Additionally, this relates to a method of producing from this inbred, hybrid seed corn and hybrid plants with seeds from such hybrid seed. More particularly, this invention relates to the unique combination of traits that combine in corn line G07-NPID4480.

Generally then, broadly the present invention includes an inbred corn seed designated G07-NPID4480. This seed produces a corn plant.

The invention also includes the tissue culture of regenerable cells of G07-NPID4480 wherein the cells of the tissue culture regenerates plants capable of expressing the genotype of G07-NPID4480. The tissue culture is selected from the group consisting of leaf, pollen, embryo, root, root tip, guard cell, ovule, seed, anther, silk, flower, kernel, ear, cob, husk and stalk, cell and protoplast thereof. The corn plant regenerated from G07-NPID4480 or any part thereof is included in the present invention. The present invention includes regenerated corn plants that are capable of expressing G07-NPID4480's genotype, phenotype or mutants or variants thereof.

The invention extends to hybrid seed produced by planting, in pollinating proximity which includes using preserved maize pollen as explained in U.S. Pat. No. 5,596,838 to Greaves, seeds of corn inbred lines G07-NPID4480 and another inbred line if preserved pollen is not used; cultivating corn plants resulting from said planting; preventing pollen production by the plants of one of the inbred lines if two are employed; allowing cross pollination to occur between said inbred lines; and harvesting seeds produced on plants of the selected inbred. The hybrid seed produced by hybrid combination of plants of inbred corn seed designated G07-NPID4480 and plants of another inbred line are apart of the present invention. This inventions scope covers hybrid plants and the plant parts including the grain and pollen grown from this hybrid seed.

The invention further includes a method of hybrid F1 production. A first generation (F1) hybrid corn plant produced by the process of planting seeds of corn inbred line G07-NPID4480; cultivating corn plants resulting from said planting; permitting pollen from another inbred line to cross pollinate inbred line G07-NPID4480; harvesting seeds produced on plants of the inbred; and growing a harvested seed are part of the method of this invention.

The present invention also encompasses a method of introducing at least one targeted trait into maize inbred line comprising the steps of: (a) crossing plant grown from the present invention seed which is the recurrent parent, representative seed of which has been deposited, with the donor plant of another maize line that comprises at least one target trait selected from the group consisting of male sterility, herbicide resistance, insect resistance, disease resistance, amylose starch, and waxy starch to produce F1 plants; (b) selecting from the F1 plants that have at least one of the targeted traits, forming a pool of progeny plants with the targeted trait; (c) crossing the pool of progeny plants with the present invention which is the recurrent parent to produce backcrossed progeny plants with the targeted trait; (d) selecting for backcrossed progeny plants that have at least one of the target traits and physiological and morphological characteristics of maize inbred line of the recurrent parent, listed in Table 1 forming a pool of selected backcrossed progeny plants; and (e) crossing the selected backcrossed progeny plants to the recurrent parent and selecting from the resulting plants for the targeted trait and physiological and morphological characteristics of maize inbred line of the recurrent parent, listed in Table 1 and reselecting from the pool of resulting plants and repeating the crossing to the recurrent parent and selecting step in succession to form a plant that comprise the desired trait and all of the physiological and morphological characteristics of maize inbred line of the recurrent parent if the present invention listed in Table 1 as determined at the 5% significance level when grown in the same environmental conditions.

This method and the following method of introducing traits can be done with less backcrossing events if the trait and/or the genotype of the present invention are selected for or identified through the use of markers. SSR, microsatellites, SNP and the like decrease the amount of breeding time required to locate a line with the desired trait or traits and the characteristics of the present invention. Backcrossing in two or even three traits (for example the glyphosate, Europe Corn Borer, Corn Rootworm resistant genes) is routinely done with the use of marker assisted breeding techniques. This introduction of transgenes or mutations into a maize line is often called single gene conversion. Although, presently more than one gene particularly transgenes or mutations which are readily tracked with markers can be moved during the same "single gene conversion" process, resulting in a line with the addition of more targeted traits than just the one, but still having the characteristics of the present invention plus those characteristics added by the targeted traits.

The method of introducing a desired trait into maize inbred line comprising:

(a) crossing a plant grown from the seed of the present invention, (representative seed on deposit) this plant being the recurrent parent, with at least one plant of another maize line that comprises at least one target trait selected from the group consisting of nucleic acid encoding an enzyme selected from the group consisting of phytase, stearyl-ACP desaturase, fructosyltransferase, levansucrase, amylase, invertase and starch branching enzyme, starch synthase, debranching enzyme, this plant being the donor parent to produce F1 plants; (b) selecting for at least one of the targeted trait from the F1 plants, (c) forming a pool of progeny plants with the target trait; (d) crossing the progeny plants with the recurrent parent to produce backcrossed progeny plants; (e) selecting from the backcrossed progeny plants that have at least one of the target traits and the physiological and morphological characteristics of maize inbred line of the present invention f) forming a new pool of backcrossed progeny plants; and repeating the step of crossing the new pool of backcrossed progeny plant with the recurrent parent and selecting for the targeted trait and the recurrent parent's characteristics until the selected plant is essentially the recurrent parent with the targeted trait or targeted traits. This selection and crossing may take 1, 2, 3, 4, 5, 6 or more backcrosses. Marker assisted breeding may limit the need for numerous backcrosses.

The inbred line and seed of the present invention are employed to carry the agronomic package into the hybrid. Additionally, the inbred line is often carrying transgenes that are introduced in to the hybrid seed.

Likewise included is a first generation (F1) hybrid corn plant produced by the process of planting seeds of corn inbred line G07-NPID4480; cultivating corn plants resulting from said planting; permitting pollen from inbred line G07-NPID4480 to cross pollinate another inbred line; harvesting seeds produced on plants of the inbred; and growing a plant from such a harvested seed.

A number of different techniques exist which are designed to avoid detasseling in maize hybrid production. Some examples are switchable male sterility, lethal genes in the pollen or anther, inducible male sterility, male sterility genes with chemical restorers. There are numerous patented means of improving upon the hybrid production system. Some examples include U.S. Pat. No. 6,025,546, which relates to the use of tapetum-specific promoters and the barnase gene to produce male sterility; U.S. Pat. No. 6,627,799 relates to modifying stamen cells to provide male sterility. Therefore, one aspect of the current invention concerns the present invention comprising one or more gene(s) capable of restoring male fertility to male-sterile maize inbreds or hybrids and/or genes or traits to produce male sterility in maize inbreds or hybrids.

The inbred corn line G07-NPID4480 and at least one transgene adapted to give G07-NPID4480 additional and/or altered phenotypic traits are within the scope of the invention. Such transgenes are usually associated with regulatory elements (promoters, enhancers, terminators and the like). Presently, transgenes provide the invention with traits such as insect resistance, herbicide resistance, disease resistance, increased or deceased starch or sugar or oil, increased or decreased life cycle or other altered traits.

The present invention includes inbred corn line G07-NPID4480 and at least one transgene adapted to give G07-NPID4480 modified starch traits. Furthermore this invention includes the inbred corn line G07-NPID4480 and at least one mutant gene adapted to give modified starch, acid or oil traits, i.e. waxy, amylose extender or amylose desaturase and mutant genes encoding starch synthase, starch branching and starch debranching enzymes and amylase. The present invention includes the inbred corn line G07-NPID4480 and at least one transgene: a Bt (*bacillus thuringiensis*), Cry or VIP gene, the bar or pat gene encoding Phosphinothricin acetyl Transferase, gdhA, GOX, VIP (vegative insecticidal protein), EPSP encoding gene, low phytic acid producing gene, and zein. The inbred corn line G07-NPID4480 and at least one transgene useful as a selectable marker or a screenable marker is covered by the present invention.

A tissue culture of the regenerable cells of hybrid plants produced with use of G07-NPID4480 genetic material is covered by this invention. A tissue culture of the regenerable cells of the corn plant produced by the method described above is also included.

DEFINITIONS

In the description and examples, which follow, a number of terms are used. In order to provide a clear and consistent understanding of the specifications and claims, including the scope to be given such terms, the following definitions are provided.

Early Season Trait Codes

Emergence (EMRGR) or (Emerge): Recorded when 50% of the plots in the trial are at V1 (1 leaf collar) growth stage.

1=All plants have emerged and are uniform in size

3=All plants have emerged but are not completely uniform

5=Most plants have emerged with some just beginning to break the soil surface, noticeable lack of uniformity 7=Less than 50% of the plants have emerged, and lack of uniformity is very noticeable 9=A few plants have emerged but most remain under the soil surface.

Seedling Growth (SVGRR) or (Vigor): Recorded between V3 and V5 (3-5 leaf stage) giving greatest weight to seedling plant size and secondary weight to uniform growth.

1=Large plant size and uniform growth

3=Acceptable plant size and uniform growth

5=Acceptable plant size and might be a little non-uniform

7=Weak looking plants and non-uniform growth

9=Small plants with poor uniformity

Purpling (PRPLR): Emergence and/or early growth rating. Purpling is more pronounced on the under sides of leaf blades especially on midribs.

1=No plants showing purple color

3=30% plants showing purple color

5=50% plants showing purple color

7=70% plants showing purple color

9=90+% plants showing purple color

Herbicide Injury (HRBDR) List the herbicide type, which is being rated. Then rated each hybrid/variety injury as indicated below.

1=No apparent reduction in biomass or other injury symptoms

5=Moderate reduction in biomass with some signs of sensitivity

9=Severe reduction in biomass with some mortality

Mid-Season Traits Codes

Heat Units to 50% Silk (HU5SN) or (S50): Recorded the day when 50% of all plants within a plot show 2 cm or more silk protruding from the ear. Converted days to accumulated heat units from planting.

Heat units to 50% Pollen Shed (HUPSN) or (P50): Recorded the day when 50% of all plants within a plot are shedding pollen. Converted days to accumulated heat units from planting.

Plant Height in cm (ERHTN) or (Pltht): After pollination, recorded average plant height of each plot. Measured from ground to base of leaf node. Three or more locations recorded.

Root Lodging Early % (ERTLP): Early root lodging occurs up to about two weeks after flowering and usually involves goosenecking. Counted the number of root lodged plants and converted to percentage. For Field Evaluation Test plots (FET), recorded lodged plants out of 50 plants from two locations in each hybrid strip, sum, and record percentage.

Foliar Disease (LFDSR): Foliar disease ratings taken one month before harvest through harvest. The predominant disease should be listed in the trial information and individual hybrid ratings should be given.

1=No lesions to two lesions per leaf.

3=A few scattered lesions on the leaf. About five to ten percent of the leaf surface is affected.

5=A moderate number of lesions are on the leaf. About 15 to 20 percent of the leaf surface is affected.

7=Abundant lesions are on the leaf. About 30 to 40 percent of the leaf surface is affected.

9=Highly abundant lesions (>50 percent) on the leaf. Lesions are highly coalesced. Plants may be prematurely killed.

The following are disease definitions (ratings based on a 1-9 scale with a one rating indicating most resistance and a nine rating indicating most susceptible):

| | |
|---|---|
| Common Rust (CR) | Eye Spot (ES) |
| Gray Leaf Spot (GLS) | Northern Corn Leaf Blight (NCLB) |
| Stewart's Bacterial Wilt (SBW) | Southern Corn Leaf Blight (SCLB) |
| Southern Rust (SR) | Corn Virus Complex (CVC) |

Preharvest Trait Codes

Final Stand (FS): count of plants per plot after thinning.

Heat units to Black Layer (HUBLN): Recorded the day when 50% of all plants within a plot reach black layer stage. Converted days to accumulated heat units from planting. Notes taken on border rows of four-row plots.

Harvest Population (HAVPN): Counted the number of plants in yield rows, excluding tillers, in each plot. For FET plots, count a thousandth of an acre two times and record the average.

Barren Plants (BRRNP): Counted the number of plants in yield rows having no ears and/or abnormal ears with less than 50 kernels. For FET plots, counted barren plants out of 50 from two locations in each hybrid strip, sum, and record the percentage. Data collected on entire trial.

Dropped Ears (DROPP) or (% DE): Counted the numbers of ears lying on the ground in yield rows. For FET plots, count dropped ears from the area of 50 plants from two locations in each hybrid strip, sum, and record the percentage.

Stalk Lodging % (STKLP) or (% SL): Stalk lodging will be reported as number of plants broken below the ear without pushing, excluding green snapped plants. Record trials with approximately five percent or more average stalk lodging. Counted the number of broken plants in yield rows and converted to percent. For FET plots, counted stalk lodged plants out of 50 from two locations in each hybrid strip, sum, and recorded the percentage.

Root Lodging Late % (LRTLP) or (% LateRL): Late root lodging can usually start to occur about two weeks after flowering and involves lodging at the base of the plant. Plants leaning at a 30-degree angle or more from the vertical are considered lodged. Counted the number of root lodged plants in yield rows and converted to percent. For FET plots, counted root lodged plants out of 50 from two locations in each hybrid strip, sum, and record the percentage.

Push Test for Stalk and Root Quality on Erect Plants % (PSTSP) or (% Push): The push test is applied to trials with approximately five percent or less average stalk lodging. Plants are pushed that are not root lodged or broken prior to the push test. Standing next to the plant, the hand is placed at the top ear and pushed to arm's length. Push one of the border rows (four-row small plot) into an adjacent plot border row. Counted the number of plants leaning at a 30-degree angle or more from the vertical, including plants with broken stalks prior to pushing, did not count plants that have strong rinds that snap rather than bend over easily. For FET plots, push 50 plants from two interior locations of each hybrid strip, sum, and record the percentage. The goal of the push test is to identify stalk rot and stalk lodging potential, NOT ECB injury. If ECB injury was present, only did a push test on the ECB trials.

Data may be collected in the following manner:

PUSXN: Push ten plants and enter the number of plants that do not remain upright.

PSTSP: This is a percent. If you push 10 plants you can simply enter 10 times the number of plants that do not remain upright (i.e. 2=20) to get the percentage.

Intactness (INTLR) or (Plantintact):

1=Healthy appearance, tops unbroken

5=25% of tops broken

9=majority of tops broken

Plant Appearance (PLTAR): This is a visual rating based on general plant appearance taking into account all factors of intactness, pest, and disease pressure.

1=Complete plant with healthy appearance

5=plants look OK

9=Plants not acceptable

Green Snap (GRSNP) or (% Greensnap) or (% GS): Counted the number of plants in yield rows that snapped below the ear due to brittleness associated with high winds. For FET plots, count snapped plants out of 50 from two locations in each hybrid strip, sum, and record the percentage.

Stay-green (STGRP) or (% Staygreen) or (% SG): This is an assessment of the ability of a grain hybrid to retain green color as maturity approaches (taken near the time of black-layer) and should not be a reflection of hybrid maturity or leaf disease. Recorded % of green tissue.

This may be listed as a Stay Green Rating or as a percentage.

Stay Green Rating (STGRR): This is an assessment of the ability of a grain hybrid to retain green color as maturity approached (taken near the time of black layer or if major differences are noted later). This rating should not be a reflection of the hybrid maturity or leaf disease.

1=solid Green Plant

9=no green tissue

Ear/Kernel Rots (KRDSR): If ear or kernel rots are present, husk ten consecutive ears in each plot and count the number that have evidence of ear or kernel rots, multiply by 10, and round up to the nearest rating as described below. Identify and recorded the disease primarily responsible for the rot.

1=No rots, 0% of the ears infected.

3=Up to 10% of the ears infected.

5=11 to 20% of the ears infected.

7=21 to 35% of the ears infected.

9=36% or more of the ears infected.

Grain Quality (GRQUR): Husked back several ears after black layer stage and observed kernel cap integrity and relative amount of soft starch endosperm along the sides of kernels.

1=smooth kernel caps and or 10% or less soft starch

3=slight kernel wrinkles and or 30% soft starch

7=moderate kernel wrinkles and or 70% soft starch

9=severe kernel wrinkled and or 90% or more soft starch

Preharvest Hybrid Characteristics

Ear Shape Slender, Semi-Blocky, Blocky

DESHR:

1=Blocky

5=Semi-blocky

9=Slender

Ear Type Fixed, Semi-Fixed, Flex (Home location: Thin outside row, every other plant for half of row.)

EARFR:

1=Flex

5=Semi-flex

9=Fixed

Husk Cover Short, Medium, Long

HSKCR:

1=Long

5=Medium

9=Short

Kernel Depth Shallow, Medium, Deep

KRLNR:

1=Deep

5=Medium

9=Short (shallow)

Shank Length Short, Medium, Long

SHLNR:

1=Short

5=Medium

9=Long

Cob Color (COBCR):

1=White

5=Pink

9=Dark Red

Kernel Row Number: Enter average of 3 ears (KRRWN): The average number of kernel rows on 3 ears.

Cob diameter (COBDR): Cob diameter to be taken with template.

1: small

5: Medium

9: Large

Corn: Harvest Trait Codes

Endosperm Type: categorized as one of the following: normal maize starch, high amylase, sweet, waxy starch, high protein, high lysine, high oil, hard endosperm.

Number of Rows Harvested (NRHAN)

Plot Width (RWIDN)

Plot Length (RLENN)

Yield Lb/Plot (YGSMN)

Test Weight in Lb/Bu (TSTWN) or (TWT)

Moisture % (MST_P) or (Moist)

Adjusted Yield in Bu/A (YBUAN)—entered or calculated

EARAR—is the Ear Size Uniformity/Ear Appearance rating

CRDSR—stands for Crown Rot

Insect Ratings

ECB1R—is European Corn Borer (ECB) rating for leaf damage. The rating is on a scale of 1-9 with 1 meaning that there is no damage.

ECB2R—is European Corn Borer (ECB) second generation ($2^{nd}$ Gen.) rating for damage. This rating is a visual rating on a scale of 1-9 with 1 meaning that there is no damage.

Color Traits

Anther color is yellow; if any other color is shown it is recorded as Other. Kernel crown color is white, yellow, orange; if any other color is shown then the color is indicated as Other. Glume ring color is listed as red/purple; if any other color is shown or if the ring color is inconsistent then Other/Absent is recorded. Brace Root Color is listed as green, reddish, purplish; if any other color is shown or if the color is inconsistent then Other is recorded.

| Color Choices: |
| --- |
| 1. light green |
| 2. medium green |
| 3. dark green |
| 4. very dark green |
| 5. green-yellow |
| 6. pale yellow |
| 7. yellow |
| 8. yelow-orange |
| 9. salmon |
| 10. pink-orange |
| 11. pink |
| 12. light red |
| 13. cherry red |
| 14. red |

| Color Choices: |
| --- |
| 15. red and white |
| 16. pale purple |
| 17. purple |
| 18. colorless |
| 19. white |
| 20. white capped |
| 21. buff |
| 22. tan |
| 23. brown |
| 24. bronze |
| 25. variegated (describe) |
| 26. other (describe) |

| Form # | ABR. | Description | Input Value |
| --- | --- | --- | --- |
| A1 | EMRGN | Final number of plants per plot | # |
| A2 | REGNN | Region Developed: 1. Northwest 2. Northcentral 3. Northeast 4. Southeast 5. Southcentral 6. Southwest 7. Other | # |
| A3 | CRTYN | Cross type: 1. sc 2. dc 3. 3w 4. msc 5. m3w 6. inbred 7. rel. line 8. other | # |
| A4 | KRTPN | Kernel type: 1. sweet 2. dent 3. flint 4. flour 5. pop 6. ornamental 7. pipecorn 8. other | # |
| A5 | EMERN | Days to Emergence EMERN | #Days |
| B1 | ERTLP | % Root lodging: (before anthesis): | #% |
| B2 | GRSNP | % Brittle snapping: (before anthesis): | #% |
| C1 | TBANN | Tassel branch angle of 2nd primary lateral branch (at anthesis): | degree |
| C10 | HUPSN | Heat units to 50% pollen shed: (from emergence) | #HU |
| C11 | SLKCN | Silk color: | #/Munsell value |
| C12 | HU5SN | Heat units to 50% silk: (from emergence) | #HU |
| C13 | DSAZN | Days to 50% silk in adapted zone: | #Days |
| C14 | HU9PN | Heat units to 90% pollen shed: (from emergence) | #HU |
| C15 | HU19N | Heat units from 10% to 90% pollen shed: | #HU |
| C16 | DA19N | Days from 10% to 90% pollen shed: | #Days |
| C2 | LSPUR | Leaf sheath pubescence of second leaf above the ear (at anthesis) 1-9 (1 = none): | # |
| C3 | ANGBN | Angle between stalk and 2nd leaf above the ear (at anthesis): | degree |
| C4 | CR2LN | Color of 2nd leaf above the ear (at anthesis): | #/Munsell value |
| C5 | GLCRN | Glume Color: | #/Munsell value |
| C6 | GLCBN | Glume color bars perpendicular to their veins (glume bands): 1. absent 2. present | # |
| C7 | ANTCN | Anther color: | #/Munsell value |
| C8 | PLQUR | Pollen Shed: 1-9 (0 = male sterile) | # |
| C9 | HU1PN | Heat units to 10% pollen shed: (from emergence) | #HU |
| D1 | LAERN | Number of leaves above the top ear node: | # |
| D10 | LTBRN | Number of lateral tassel branches that originate from the central spike: | # |
| D11 | EARPN | Number of ears per stalk: | # |
| D12 | APBRR | Anthocyanin pigment of brace roots: 1. absent 2. faint 3. moderate 4. dark | # |
| D13 | TILLN | Number of tillers: | # |
| D14 | HSKCN | Husk color 25 days after 50% silk: (fresh) | #/Munsell value |
| D2 | MLWVR | Leaf marginal waves: 1-9 (1 = none) | # |
| D3 | LFLCR | Leaf longitudinal creases: 1-9 (1 = none) | # |
| D4 | ERLLN | Length of ear leaf at the top ear node: | #cm |
| D5 | ERLWN | Width of ear leaf at the top ear node at the widest point: | #cm |
| D6 | PLHTN | Plant height to tassel tip: | #cm |
| D7 | ERHCN | Plant height to the top ear node: | #cm |
| D8 | LTEIN | Length of the internode between the ear node and the node above: | #cm |
| D9 | LTASN | Length of the tassel from top leaf collar to tassel tip: | #cm |
| E1 | HSKDN | Husk color 65 days after 50% silk: (dry) | #/Munsell value |

-continued

| Form # | ABR. | Description | Input Value |
|---|---|---|---|
| E10 | DSGMN | Days from 50% silk to 25% grain moisture in adapted zone: | #Days |
| E11 | SHLNN | Shank length: | #cm |
| E12 | ERLNN | Ear length: | #cm |
| E13 | ERDIN | Diameter of the ear at the midpoint: | #mm |
| E14 | EWGTN | Weight of a husked ear: | #gm |
| E15 | KRRWR | Kernel rows: 1. indistinct 2. distinct | # |
| E16 | KRNAR | Kernel row alignment: 1. straight 2. slightly curved 3. curved | # |
| E17 | ETAPR | Ear taper: 1. slight 2. average 3. extreme | # |
| E18 | KRRWN | Number of kernel rows: | # |
| E19 | COBCN | Cob color: | #/Munsell value |
| E2 | HSKTR | Husk tightness 65 days after 50% silk: 1-9 (1 = loose) | # |
| E20 | COBDN | Diameter of the cob at the midpoint: | #mm |
| E21 | YBUAN | Yield: | #kg/ha |
| E22 | KRTEN | Endosperm type: 1. sweet 2. extra sweet 3. normal 4. high amylose 5. waxy 6. high protein 7. high lysine 8. super sweet 9. high oil 10. other | 3 |
| E23 | KRCLN | Hard endosperm color: | #/Munsell value |
| E24 | ALECN | Aleurone color: | #/Munsell value |
| E25 | ALCPR | Aleurone color pattern: 1. homozygous 2. segregating | # |
| E26 | KRLNN | Kernel length: | #mm |
| E27 | KRWDN | Kernel width: | #mm |
| E28 | KRDPN | Kernel thickness: | #mm |
| E29 | K1KHN | 100 kernel weight: | #gm |
| E3 | HSKCR | Husk extension: 1. short (ear exposed) 2. medium (8 cm) 3. long (8-10 cm) 4. very long (>10 cm) | # |
| E30 | KRPRN | % round kernels on 13/64 slotted screen: | #% |
| E4 | HEPSR | Position of ear 65 days after 50% silk: 1. upright 2. horizontal 3. pendent | # |
| E5 | STGRP | Staygreen 65 days after anthesis: 1-9 (1 = worst) | # |
| E6 | DPOPP | % dropped ears 65 days after anthesis: | % |
| E7 | LRTRP | % root lodging 65 days after anthesis: | % |
| E8 | HU25N | Heat units to 25% grain moisture: (from emergence) | #HU |
| E9 | HUSGN | Heat units from 50% silk to 25% grain moisture in adapted zone: | #HU |

DETAILED DESCRIPTION OF THE INVENTION

G07-NPID4480 is shown in comparison with NP2171.

The inbred provides uniformity and stability within the limits of environmental influence for traits as described in the Variety Description Information (Table 1) that follows.

The inbred has been produced through a dihaploid system or is self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in G07-NPID4480.

The best method of producing the invention is by planting the seed of G07-NPID4480 which is substantially homozygous and self-pollinating or sib pollinating the resultant plant in an isolated environment, and harvesting the resultant seed.

TABLE 1

G07-NPID4480
VARIETY DESCRIPTION INFORMATION

1 Type: Dent
2 Region Best Adapted: Broadly adapted

| MG Group | Maturity Range | Hybrid RM (estimate) |
|---|---|---|
| 4 | 98-102 | 103 |

3a Plant Color Traits

| AntherClr | GlumeClr | SilkClr | BraceRtClr | CobClr | KernelClr |
|---|---|---|---|---|---|
| Green | Green | Yellow | Moderate | White | Yellow |

TABLE 1-continued

G07-NPID4480
VARIETY DESCRIPTION INFORMATION

3b Plant Traits Full definitions listed above.

| | Plot Quality Rating PLTQR | HU to 50% Silk HU5SN | HU to 50% Pollen Shed HUPSN | Seedling Vigor: 3-5 leaf SVGRR | Ear Height in cm ERHTN | Root lodging Late % LRTLP | Plant Height - PLHTN | Stand # STD_N |
|---|---|---|---|---|---|---|---|---|
| G07-NPID4480 | 6.5 | 1342.9 | 1347.8 | 5.0 | 74.0 | 0.0 | 177.5 | 48.3 |

| | Grain Yield at Std Mst % - YGSMN | Harvest Population HAVPN | Leaf Scrolling | Root Lodging Early % ERTLP | Greensnap % GRSNP | HU to 10% Pollen Shed HU1PN | HU to 90% Pollen Shed HU9PN | Stay Green % STGRP |
|---|---|---|---|---|---|---|---|---|
| G07-NPID4480 | 40.0 | 83651.0 | 1.0 | 0.0 | 0.0 | 1271.5 | 1351.0 | 1.0 |

| | Rating for quantity of p PLQUR | Degrees leaf angle 2nd l ANGBN | Cob diameter at mid-poin COBDN | Drop Ears % DROPP | Ears Per plant # EARPN | Emerged Plants Prior EMRGP | Ear length ERLNN | Grain Moisture at harvest GMSTP |
|---|---|---|---|---|---|---|---|---|
| G07-NPID4480 | 3.5 | 56.3 | 21.4 | 0.0 | 1.0 | | 12.2 | 21.6 |

| | Grain weight pler plot | Husk Coverage Rating HSKCR | Husk color 65 days after HSKDN | Husk tightness (1 = very loose) HSKTR | Heat units from 10% to 90% HU19N | Kernel thickness KRDPN | Kernel length KRLNN | Number of kernel rows KRRWN |
|---|---|---|---|---|---|---|---|---|
| G07-NPID4480 | 4.8 | 2.0 | 5.0 | 8.3 | 79.5 | 7.5 | 12.0 | 14.0 |

| | Kernel type: 1 sweet; 2 KRTPN | Kernel width KRWDN | Number of leaves above t LAERN | Leaf sheath pubescence LSPUR | Tassel length from top LTASN | Number of lateral tassel LTBRN | Length of top ear internode LTEIN | Marginal waves (1 = none) MLWVR |
|---|---|---|---|---|---|---|---|---|
| G07-NPID4480 | 2.0 | 7.0 | 6.7 | 4.0 | 35.5 | 4.9 | 16.5 | |

| | Region developed: 1 NW; PREGN | Shank Length (cm) SHLNN | Stand % STD_P | Lateral tassel branch an TBANN | Tillering TILLN | Tillering % TILLP | Test Wt at Harv Mst - TWHMN | Test Weight in Std Mst |
|---|---|---|---|---|---|---|---|---|
| G07-NPID4480 | 2.0 | 5.0 | 100.0 | 36.3 | 0.0 | 0.0 | 67.8 | 71.3 |

The data provided above is often a color. The Munsell code is a reference book of color, which is known and used in the industry and by persons with ordinary skill in the art of plant breeding. The purity and homozygosity of inbred G07-NPID4480 is constantly being tracked using isozyme genotypes.

Table 2 shows a comparison between G07-NPID4480 and a comparable inbred.

G07-NPID4480 has significantly different stand and number of ears than NP2171. The present invention has significantly different percentage of discard than the comparison inbred.

TABLE 2

PAIRED INBRED COMPARISON DATA

| Year | Inbred | Stand | # Ears | Yield | % Discard | Kernels/Lb | cost of Goods |
|---|---|---|---|---|---|---|---|
| Overall | G07-NPID4480 | 41.4 | 45.1 | 83.7 | 2 | 1681.1 | 18 |
| | NP2171 | 56.5 | 58.4 | 75.1 | 5.3 | 1777.7 | 19 |
| | Diff | 12.7 | 13.4 | 8.5 | 3.3 | 96.6 | 1 |
| | #Expts | 6 | 7 | 7 | 7 | 7 | 7 |
| | Prob | 0.012** | 0.017** | 0.176 | 0.035** | 0.156 | 0.688 |

TABLE 2-continued

PAIRED INBRED COMPARISON DATA

| Year | Inbred | % Large Rounds | % Large Flats | % Med. Rounds | % Med. Flats | % Smalls |
|---|---|---|---|---|---|---|
| Overall | G07-NPID4480 | 36 | 13.7 | 24.8 | 24.2 | 1.3 |
|  | NP2171 | 25.9 | 23.7 | 26.6 | 20 | 3.9 |
|  | Diff | 10.3 | 10 | 1.8 | 4.2 | 2.7 |
|  | #Expts | 6 | 6 | 6 | 6 | 6 |
|  | Prob | 0.11 | 0.096* | 0.755 | 0.179 | 0.214 |

| Year | Inbred | % Mediums | Pollen Quant. | % Poll. Quant. | Shed Duration | % Shed Dur. |
|---|---|---|---|---|---|---|
| Overall | G07-NPID4480 | 48.8 | 391,574 | 20.7 | 175 | 96 |
|  | NP2171 | 46.6 | 443,667 | 23.7 | 143.7 | 76.7 |
|  | Diff | 2.2 | 52,093 | 3 | 37.7 | 20 |
|  | #Expts | 6 | 3 | 3 | 3 | 3 |
|  | Prob | 0.789 | 0 | 0.324 | 0.117 | 0.11 |

*.05 < Prob <= .10
**.01 < Prob <= .05
***.00 < Prob <= .01

Table 3 shows the GCA (General Combining Ability) estimates of G07-NPID4480 compared with the GCA estimates of the other inbreds. The estimates show the general combining ability is weighted by the number of experiment/location combinations in which the specific hybrid combination occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data is from our company's and other companies' hybrids which are commercial products and pre-commercial hybrids, which were grown in the same sets and locations.

TABLE 3

| Parent1 | Parent2 | N05 | N06 | N07 | N | Yield | Moist | TWT | PCTERL | PCTSL | PCTPUSH | PLTLRL | PCTDE |
|---|---|---|---|---|---|---|---|---|---|---|---|---|---|
| G07-NPID4480 | | | | 15 | 15 | −6.67 | 1.43 | −0.16 | | −5.94 | | −5.38 | 0 |
| G07-NPID4480 | | | | 8 | 8 | −5.72 | −1.01 | 0.14 | | 0.36 | | | |
| G07-NPID4480 | | | | 12 | 12 | 15.03 | 0.44 | 0.06 | | −6.63 | | 5.39 | |
| G07-NPID4480 | | | | 11 | 11 | 16.31 | −1.74 | −0.03 | | −0.26 | | 2.36 | |
| G07-NPID4480 | | | | 16 | 16 | −10.9 | 1.23 | 0.25 | | −0.61 | | 2.72 | |
| G07-NPID4480 | | | | 15 | 15 | −5.65 | 1.4 | 0.63 | | −4.53 | | −10.7 | |
| G07-NPID4480 | | | 38 | 44 | 82 | 6.09 | 1.06 | 0.22 | 5.03 | −0.57 | −18.4 | −0.2 | 0.03 |
| G07-NPID4480 | | | | 12 | 12 | −1.99 | −1.03 | 0.04 | | 1.38 | | 5.39 | |
| G07-NPID4480 | | | | 14 | 14 | −10.32 | 0.32 | −0.17 | | −11.8 | | −1.61 | |
| G07-NPID4480 | | | | 15 | 15 | −8.24 | −0.12 | 0.03 | | −2.42 | | −14.63 | |
| G07-NPID4480 | | | | 14 | 14 | −0.84 | −0.71 | −0.22 | | −24.76 | | −8.99 | 0 |
| G07-NPID4480 | | | | 12 | 12 | 6.86 | −1.96 | 0.04 | | 1.38 | | 0.84 | |
| G07-NPID4480 | | | | 12 | 12 | −6.08 | −0.06 | 0.32 | | 1.38 | | 5.39 | |
| G07-NPID4480 | | | | 11 | 11 | −4.36 | −0.21 | −0.12 | | −6.32 | | 0.84 | |
| G07-NPID4480 | | | | 12 | 12 | −14.44 | −1.83 | −0.06 | | 1.38 | | 5.39 | |
| G07-NPID4480 | | | | 12 | 12 | −5.37 | −1.61 | −0.07 | | 0.4 | | −0.95 | |
| G07-NPID4480 | | | | 16 | 16 | 12.28 | −1.75 | −0.29 | | −2.04 | | −8.37 | |
| G07-NPID4480 | | | | 12 | 12 | 10.2 | −1.43 | 0.13 | | −5.09 | | 9.66 | |
| G07-NPID4480 | | | | 12 | 12 | −3.93 | −0.92 | −0.4 | | −1.15 | | 2.73 | |
| G07-NPID4480 | | | | 11 | 11 | 13.99 | −0.56 | 0.08 | | 1.84 | | −4.21 | |
| G07-NPID4480 | | | | 11 | 11 | −7.86 | −1.89 | −0.09 | | 1.38 | | 3.87 | |
| G07-NPID4480 | | | | 12 | 12 | 0.44 | −2.46 | −0.11 | | 1.38 | | 5.39 | |
| G07-NPID4480 | | | | 10 | 10 | 2.42 | −2.32 | −0.02 | | 1.09 | | −0.84 | |
| G07-NPID4480 | | | | 16 | 16 | −12.66 | −0.28 | 0.11 | | −4.88 | | −0.26 | |
| G07-NPID4480 | | | | 15 | 15 | 18.98 | −1.44 | −0.24 | | 1.14 | | −21.17 | |
| G07-NPID4480 | | | | 14 | 14 | −5.23 | −0.79 | −0.03 | | 0.81 | | −3.29 | |
| XR = | | | | 14 | 427 | 0.63 | −0.33 | 0.04 | 5.03 | −2.42 | −18.4 | −4.29 | 0.02 |
| XH = | | | | 14 | 26 | −0.29 | −0.7 | 0 | 5.03 | −2.43 | −18.4 | −1.23 | 0.01 |
| XT = | | | | 14 | 1 | 6.09 | 1.06 | 0.22 | 5.03 | −0.57 | −18.4 | −0.2 | 0.03 |

| Parent1 | Parent2 | FS | PCTSG | PCTGS | Pop | Emerge | Vigor | PlantIntact | HUS50 | HUBL | Pltht | Earht |
|---|---|---|---|---|---|---|---|---|---|---|---|---|
| G07-NPID4480 | | 0.03 | | | 16.13 | | | | | | −11.25 | 0 |
| G07-NPID4480 | | 0 | | | 0 | | −1.56 | | −1.56 | | −9.44 | −23.89 |
| G07-NPID4480 | | 0.03 | | | 13.44 | | −0.89 | | −3.33 | | 14.44 | 8.33 |
| G07-NPID4480 | | −0.06 | | | −26.89 | | 1.11 | | 2.67 | | 14.44 | 10.83 |

TABLE 3-continued

| | | | | | | | | | | | |
|---|---|---|---|---|---|---|---|---|---|---|---|
| G07-NPID4480 | | −0.69 | | | −335.78 | | | | | −7.81 | −14.38 |
| G07-NPID4480 | | −0.64 | | | −308.15 | | | | | 27.19 | −14.38 |
| G07-NPID4480 | | −0.13 | 9.89 | 1.17 | −61.12 | 0.16 | 0.31 | −0.4 | −12.51 −2523.1 | 8.19 | 0.18 |
| G07-NPID4480 | | −0.06 | | | −26.89 | | | | | 4.44 | 8.33 |
| G07-NPID4480 | | −0.16 | | | −77.44 | −0.05 | −0.89 | −1.33 | 35.58 | 9.5 | 10.5 |
| G07-NPID4480 | | −0.16 | | | −77.44 | −1.05 | | | 48.98 | 2 | −9.5 |
| G07-NPID4480 | | −0.36 | | | −172.86 | | | | | | |
| G07-NPID4480 | | 0.19 | | | 94.11 | | 1.11 | −2.33 | | 9.44 | 3.33 |
| G07-NPID4480 | | −0.56 | | | −268.89 | | −0.89 | −1.33 | | 11.94 | 3.33 |
| G07-NPID4480 | | −0.22 | | | −107.56 | | −0.89 | −1.33 | | 4.44 | 5.83 |
| G07-NPID4480 | | 0.11 | | | 53.78 | | −0.89 | −1.33 | | −15.56 | −9.17 |
| G07-NPID4480 | | −0.22 | | | −107.56 | | 2 | 1.33 | | 12.48 | −8.42 |
| G07-NPID4480 | | −0.34 | | | −166.74 | | | 1.86 | 7.77 | 5.89 | 10 |
| G07-NPID4480 | | −0.22 | | | −107.56 | | 0 | −0.67 | | −10.02 | −10.92 |
| G07-NPID4480 | | 0.13 | | | 62.74 | | 1.6 | 0.2 | | 9.25 | 4.75 |
| G07-NPID4480 | | 0.35 | | | 168.15 | | | 0.57 | | 15.89 | −2.5 |
| G07-NPID4480 | | −0.22 | | | −107.56 | | −0.89 | 2.67 | | −0.56 | −1.67 |
| G07-NPID4480 | | −0.06 | | | −26.89 | | −0.89 | 2.67 | | 11.94 | 8.33 |
| G07-NPID4480 | | −0.22 | | | −107.56 | | −1.11 | −1.78 | | 1.94 | −0.56 |
| G07-NPID4480 | | 2.47 | | | 1194.54 | | | −0.14 | 7.77 | −4.11 | 0 |
| G07-NPID4480 | | −0.18 | | | −89.12 | | | 1.36 | 55.77 | 24.29 | 5 |
| G07-NPID4480 | | 1.09 | | | 526.81 | | | 0.86 | | 4.29 | −10 |
| | XR = | −0.02 | 9.89 | 1.17 | −7.57 | −0.02 | 0.1 | −0.16 | 2.05 −2523.1 | 6.07 | 0.12 |
| | XH = | 0 | 9.89 | 1.17 | −1.78 | −0.31 | −0.18 | −0.07 | 23.89 −2523.1 | 5.33 | −1.06 |
| | XT = | −0.13 | 9.89 | 1.17 | −61.12 | 0.16 | 0.31 | −0.4 | −12.51 −2523.1 | 8.19 | 0.18 |

XR = GCA Estimate: Weighted by Expt
XH = GCA Estimate: Weighted by Parent2
XT = Same as XH but using only those parent2 with two years of data Table 4 shows the inbred G07-NPID4480 in hybrid combination, in comparison with another hybrid 2, which is adapted for the same region of the Corn Belt. When in this hybrid combination, the G07-NPID4480 hybrid carries significantly different stay green and vigor in comparison to the other hybrid. There is a significant difference in the number of heat units required to reach 50% silk and 50% pollen between the two hybrids.

TABLE 4

PAIRED HYBRID COMPARISON DATA

| Year | Hybrid Hybrid | Yield Yield | Moist Moist | Test Wt TWT | EarlyRtLdg % SL | StalkLdg % Push | PushTest % LateRL |
|---|---|---|---|---|---|---|---|
| Overall | G07-NPD4480/ Hybrid | 201.0 | 19.4 | 56.3 | 3.8 | 45.0 | 2.1 |
| | Hybrid 2 | 184.2 | 19.0 | 56.7 | 7.9 | 37.5 | 1.4 |
| | # Expts | 38.0 | 38.0 | 37.0 | 17.0 | 2.0 | 7.0 |
| | Diff | 16.9 | 0.3 | 0.4 | 4.2 | 7.5 | 0.6 |

| Year | Hybrid | % EarlyRL | % DE | FS | % StayGreen | % Greensnap | % Barren |
|---|---|---|---|---|---|---|---|
| Overall | G07-NPD4480/ Hybrid | 0.0 | 0.0 | 64.1 | 16.7 | 1.2 | 0.7 |
| | Hybrid 2 | 1.7 | 0.0 | 64.4 | 25.0 | 3.1 | 5.3 |
| | #Expts | 3.0 | 3.0 | 38.0 | 9.0 | 2.0 | 3.0 |
| | Diff | 1.7 | 0.0 | 0.4 | 8.3 | 1.9 | 4.7 |
| | Prob | 0.4 | | 0.4 | 0.024** | 0.1 | 0.3 |

| Year | Hybrid | Emerge | Vigor | Heatunits to S50 | Heatunits to P50 | Earht | Pltht |
|---|---|---|---|---|---|---|---|
| Overall | G07-NPD4480/ Hybrid | 4.2 | 3.3 | 1288.0 | 1275.0 | 111.3 | 292.0 |
| | Hybrid 2 | 4.5 | 4.3 | 1307.0 | 1297.0 | 100.4 | 285.9 |
| | #Expts | 12.0 | 11.0 | 5.0 | 5.0 | 7.0 | 7.0 |
| | Diff | 0.3 | 1.0 | 18.6 | 21.6 | 10.9 | 6.1 |
| | Prob | 0.3 | 0.019** | 0.083* | 0.001*** | 0.3 | 0.3 |

*.05 < Prob <= .10
**.01 < Prob <= .05
***.00 < Prob <= .01

Table 5 shows the yield response of G07-NPID4480 in hybrid combination in comparison with the plants in the environment around it at the same location and in comparison with hybrid 2. The data for the present inbred and the comparison inbred is subject to errors of 14 and 20.1 respectively due to the limited number of plots.

TABLE 5

YIELD RESPONSE
Research Plots

| Hybrid | Error | # Plots | 75 | 100 | 125 | 150 | 175 | 200 |
|---|---|---|---|---|---|---|---|---|
| G07-NPID4480 Hybrid | 14 | 38 | 85 | 110 | 135 | 160 | 185 | 210 |
| Hybrid 2 | 20.1 | 129 | 60 | 87 | 114 | 140 | 167 | 194 |

This invention also is directed to methods for producing a corn plant by crossing a first parent corn plant with a second parent corn plant wherein the first or second parent corn plant is an inbred corn plant from the line G07-NPID4480. Further, both first and second parent corn plants can come from the inbred corn line G07-NPID4480 which produces a self of the inbred invention. The present invention can be employed in a variety of breeding methods which can be selected depending on the mode of reproduction, the trait, and the condition of the germplasm. Thus, any breeding methods using the inbred corn line G07-NPID4480 are part of this invention: selfing, backcrosses, hybrid production, and crosses to populations, and haploid by such old and known methods of using KWS inducers lines, Krasnador inducers, stock six material that induces haploids and anther culturing and the like.

The present invention may be useful as a male-sterile plant. Sterility can be produced by pulling or cutting tassels from the plant, detasseling, use of gametocides, use of genetic material to render the plant sterile using a CMS type of genetic control or a nuclear genetic sterility. Male sterility is employed in a hybrid production by eliminating the pollen from the seed producing parent so when in isolation from other pollen source the only available pollen is that from the second male fertile inbred planted most often in rows near the male sterile inbred.

Methods for genetic male sterility are disclosed in EPO 89/3010153.8, WO 90/08828, U.S. Pat. Nos. 4,654,465, 4,727,219, 3,861,709, 5,432,068 and 3,710,511. Gametocides which are chemicals or substances that negatively affect the pollen or at least the fertility of the pollen can be employed to provide male sterility.

Unfortunately, for hybrid production nature complicates male sterility and as a result there are self pollinated female inbred seeds in some hybrid production. Great measures are taken to avoid this inbred production in a hybrid field but it unfortunately does occur. If a hybrid bag of seed is tested with molecular markers it may be possible to detect inbred seed. If the hybrid seed is planted these inbred plants tend to be readily identifiable as runt like appearance—shorter plant, small ear, or other characteristics when the hybrid seed in a bag is planted. Self pollination of these plants produces the female inbred seed. The seed in a hybrid seed bag is not sold to the growers for breeding but to plant and produce only for use as grain and forage.

Process for producing seed comprises planting a group of seed comprising seed from a hybrid production, one of whose parents is the present invention said group, growing plants from this seed, identifying any inbred plants, selecting and pollinating the inbred plant.

A number of well known methods can be employed to identify the genotype of maize. The ability to understand the genotype of the present invention increases as the technology moves toward better markers for identifying different components within the maize genetic material. One of the oldest methods is the use of isozymes which provides a generalized footprint of the material. Other markers that were adapted to provide a higher definition profile include Restriction Fragment Length Polymorphisms (RFLPs), Amplified Fragment Length Polymorphisms (AFLPs), Random Amplified Polymorphic DNAs (RAPDs), Polymerase Chain Reaction (there are different types of primers or probes) (PCR), Microsattelites (SSRs), and Single Nucleotide Polymorphisms (SNPs) just to list a few. The use of these and a number of other markers for gathering genotype information is well understood in the industry and can be found in college textbooks such as Breeding Field Crops, Milton et. al., Iowa State University Press.

The profile of the inbred of this invention should be close to homozygous for alleles. A marker profile produced with any of the locus identifying systems known in the industry will identify a particular allele at particular loci. A F1 hybrid made from the inbred of this invention will comprise a marker profile of the sum of both of its inbred parents. At each locus the allele for the present invention and the allele for the other inbred parent should be present. Thus the profile of the present invention will permit identification of hybrids as containing the inbred parent of the present invention. To identify the female portion of the hybrid the material from the pericarp which is maternally inherited is employed. The comparison of this maternal profile with the hybrid profile will allow identification of the paternal profile. The present invention includes a maize cell that is part of an inbred or hybrid plant which includes its seed or plant part that has the marker profile of alleles of the present invention.

Marker systems are not just useful for identification of the present invention; they are also useful for breeding and trait conversion techniques. Polymorphisms in maize permit the use of markers for linkage analysis. If SSR are employed with flanking primers PCR can be used and Southern Blots can often be eliminated. Use of flanking markers and PCR and amplification of the material is well known by the industry. Primers for SSRS and mapping information are publicly available through the help of the USDA at Maize GDB on the web.

Marker profiles of this invention can identify essentially derived varieties or progeny developed with the inbred in its ancestry. This inbred may have progeny identified by having a molecular marker profile of at least 25%, to 40%, 45%, 50% to 80% (which includes each of the numbers between these two percentages), 81%, 82%, 83%, 84%, 85%, 86%, 87%, 88%, 89%, 90%, 91%, 92%, 93%, 94%, 95%, 96%, 97%, 98%, 99% genetic contribution of the present inbred invention, as measured by either percent identity or percent similarity.

The present invention may have a new locus or trait introgressed through direct transformation or backcrossing or marker assisted breeding. A backcross conversion or locus conversion both refer to a product of a backcrossing program.

DNA sequences are introduced through backcrossing (Hallauer et al. in Corn and Corn Improvement, Sprague and Dudley, Third Ed. 1998), with PH8JV utilized as the recurrent parent.

When the present inbred is used as a recurrent parent in a breeding program it is often referred to as backcrossing. Backcrossing is often employed to introgression a desired trait or trait(s), either transgenic or nontransgenic, into the recurrent parent. A plant may be selected with the trait or the desired locus in one or more backcrosses. If markers are employed to assist in selection the number of backcrosses needed to recover the recurrent parent with the desired trait or locus can be relatively few two or three. However, three, four, five or more backcrosses are often required to produce the desired inbred with the gene or loci conversion in place. The number of backcrosses needed for a trait introgression is often linked to the genetics of the trait. Multigenic traits, recessive alleles, unlinked traits, how the traits are inherited all will play a role in the number of backcrosses that may be necessary to achieve the desired backcross conversion of the inbred.

Dominant, single gene traits or traits with obvious phenotypic changes are particularly well managed in a backcrossing program. Prior to transformation and prior to markers, backcrossing was employed since at least the 1950's to alter grain color, to move mutations into inbreds—such as sugary 2, waxy, amylose extender, dull, brittle, shrunken, sugary 1, waxy (wx), shrunken-2.

In a book written by Dr. Hallauer, entitled *Corn and Corn Improvement*, published by Sprague and Dudley, 3rd Ed. (1998), the basics of backcrossing along with a number of other corn breeding methods such as recurrent or bulk or mass selection, pedigree breeding, open pollination breeding, marker assisted selection, double haploids development and breeding is taught. The ordinary corn breeder understands these breeding systems and how to apply them to the present invention; therefore, repetition of these breeding methods need not be listed within this application.

The backcrossing program is more complicated when the trait is a recessive gene. To determine the presence of the recessive gene often requires the use of additional testing to determine if the trait has been transferred. Use of markers to detect the gene reduces the complexity of trait identification in the progeny. A marker that is a SNP specific for the trait itself can be very useful in increasing the efficiency and speed of tracking a recessive trait within a backcrossing program. Mutations for the last 60 years have been backcrossed in this manner into elite germplasm.

Mutations can be induced in germplasm by the plant breeder. Mutations can result from plant or seed or pollen exposure to temperature alterations, culturing, radiation in various forms, chemical mutagens like EMS and others. Some of the mutant genes which have been identified in maize include the genotypes: waxy (wx), amylose extender (ae), dull (du), horny (h), shrunken (sh), brittle (bt), floury (fl), opaque (o), and sugary (su). Nomenclature for mutant genes is based on the effect these mutant genes have on the physical appearance, phenotype, of the kernel. It is also known that within these genotypes there are genes which produce starch with markedly different functional properties even though the phenotypes are the same. Such subspecies *have* generally been given a number after the named genotype, for example, sugary-1 (su1), sugary-2 (su2); shrunken 1 and shrunken 2. Traits such as Ht, waxy, shrunken, amylose extender, opaque, sugary 1, 2, dull, IT, IR, sterility, fertility, low phytic acid, NLB, SLB, and the like have all been introgressed into elite inbreds through backcrossing programs. The last backcross generation may be selfed if necessary to recover the inbred of interest with the introgressed trait.

All plants and plant cells produced using inbred corn line G07-NPID4480 are within the scope of this invention. The invention encompasses the inbred corn line used in crosses with other, different, corn inbreds to produce (F1) corn hybrid seeds and hybrid plants and the grain produced on the hybrid plant. This invention includes plant and plant cells, which upon growth and differentiation produce corn plants having the physiological and morphological characteristics of the inbred line G07-NPID4480.

Additionally, this maize line can, within the scope of the invention, contain: a mutant gene such as, but not limited to, amylose, amylase, sugary 1, shrunken 1, waxy, AE (amylose extender), dull, brown midrib, or imazethapyr tolerant (IT or IR™); or transgenes such as, but not limited to, insect resistant genes such as Corn Rootworm gene(s) in the event DAS-59122-7, Mir603 Modified Cry3A event, MON 89034, MON 88017 *Bacillus thuringiensis* (Cry genes) Cry34/35Ab1, Cry1A.105, PO Cry1F, Cry2Ab2, Cry1A, Cry1AB, Cry1Ac Cry3Bb1, or herbicide resistant genes such as pat gene or bar gene, EPSP, the altered protoporphyrinogen oxidase (protox enzyme) U.S. Pat. Nos. 5,767,373; 6,282,837; WO 01/12825, or disease resistant genes such as the Mosaic virus resistant gene, etc., or other trait altering genes such as lignin genes, flowering genes, oil modifying genes, senescence genes and the like. Altered carbohydrates or altered starch can include genes for enzymes that affects the synthases, branching enzymes, pullanases, debranching enzymes, isoamylases, alpha amylases, beta amylases, AGP, ADP and other enzymes which effect the amylose, amylopectin ratio or content or the branching pattern of starch. The fatty acid modifying genes can also affect starch content.

The methods and techniques for inserting, or producing and/or identifying a mutation or making or reshuffling a transgene and introgressing the trait or gene into the present invention through breeding, transformation, mutating and the like are well known and understood by those of ordinary skill in the art.

A number of different inventions exist which are designed to avoid detasseling in maize hybrid production. Some examples are switchable male sterility, lethal genes in the pollen or anther, inducible male sterility, male sterility genes with chemical restorers, sterility genes linked with a parent. U.S. Pat. No. 6,025,546 relates to the use of tapetum-specific promoters and the barnase gene. U.S. Pat. No. 6,627,799 relates to modifying stamen cells to provide male sterility. Therefore, one aspect of the current invention concerns the present invention comprising one or more gene(s) capable of restoring male fertility to male-sterile maize inbreds or hybrids.

Various techniques for breeding, moving or altering genetic material within or into the present invention (whether it is an inbred or in hybrid combination) are also known to those skilled in the art. These techniques (to list only a few) are anther culture for haploid/double haploid production, stock six, (which is a breeding/selection method using color markers and is a method that has been in use for forty years and is well known to those with skill in the art), transformation, irradiation to produce mutations, chemical or biological mutation agents and a host of other methods are within the scope of the invention. All parts of the G07-NPID4480 plant including plant cells are within the scope of this invention. The term transgenic plant refers to plants having genetic sequences, which are introduced into the genome of a plant by a transformation method and the progeny thereof. Transformation methods are means for integrating new genetic coding sequences into the plant's genome by the incorporation of these sequences into a plant through man's assistance, but not by breeding practices. The transgene once introduced into plant material and integrated stably can be moved into other germplasm by standard breeding practices.

Though there are a large number of known methods to transform plants, certain types of plants are more amenable to transformation than are others. Monocots can present some transformation challenges, however, the basic steps of transforming monocots plants have been known in the art for about 15 years. The most common method of maize transformation is referred to as gunning or microprojectile bombardment though other methods can be used. The process employs small gold-coated particles coated with DNA which are shot into the transformable material. Detailed techniques for gunning DNA into cells, tissue, callus, embryos, and the like are well known in the prior art. One example of steps that can be involved in monocot transformation are concisely outlined in U.S. Pat. No. 5,484,956 "Fertile Transgenic Zea mays Plants Comprising Heterologous DNA Encoding *Bacillus Thuringiensis* Endotoxin" issued Jan. 16, 1996 and also in U.S. Pat. No. 5,489,520 "Process of Producing Fertile Zea mays Plants and Progeny Comprising a Gene Encoding Phosphinothricin Acetyl Transferase" issued Feb. 6, 1996.

Plant cells such as maize can be transformed not only by the use of a gunning device but also by a number of different techniques. The recombinant DNA molecules of the invention can be introduced into the plant cell in a number of art-recognized ways. Those skilled in the art will appreciate that the choice of method might depend on the type of plant, i.e. monocot or dicot, targeted for transformation. Suitable methods of transforming plant cells include microinjection (Crossway et al., BioTechniques 4:320-334 (1986)), electroporation (Riggs et al, Proc. Natl. Acad. Sci. USA 83:5602-5606 (1986), *Agrobacterium* mediated transformation (Hinchee et al., Biotechnology 6:915-921 (1988)), direct gene transfer (Paszkowski et al., EMBO J. 3:2717-2722 (1984)), ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., Biotechnology 6:923-926 (1988)), protoplast transformation/regeneration methods (see U.S. Pat. No. 5,350,689 issued Sep. 27, 1994 to Ciba-Geigy Corp.), Whiskers technology (See U.S. Pat. Nos. 5,464,765 and 5,302,523) and pollen transformation (see U.S. Pat. No. 5,629,183). Also see, Weissinger et al., Annual Rev. Genet. 22:421-477 (1988); Sanford et al., Particulate Science and Technology 5:27-37 (1987) (onion); Christou et al., Plant Physiol. 87:671-674 (1988) (soybean); McCabe et al., Bio/Technology 6:923-926 (1988) (soybean); Datta et al., Bio/Technology 8:736-740 (1990) (rice); Klein et al., Proc. Natl. Acad. Sci. USA, 85:4305-4309 (1988) (maize); Klein et al., Bio/Technology 6:559-563 (1988) (maize); Klein et al., Plant Physiol. 91:440-444 (1988) (maize); Fromm et al., Bio/Technology 8:833-839 (1990); Gordon-Kamm et al., Plant Cell 2:603-618 (1990) (maize); and U.S. Pat. Nos. 5,591,616 and 5,679,558 (rice).

A further subject of the present invention are the plants which comprise transformed cells, in particular the plants regenerated from transformed cells. Regeneration is effected by any suitable process, which depends on the nature of the species as described, for example, in the references hereinabove. Patents and patent applications which are cited in particular for the processes for transforming plant cells and regenerating plants are the following: U.S. Pat. Nos. 4,459, 355, 4,536,475, 5,464,763, 5,177,010, 5,187,073, EP 267, 159, EP 604 662, EP 672 752, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442 174, EP 486 233, EP 486 234, EP 539 563, EP 674 725, WO 91/02071 and WO 95/06128.

The use of pollen, cotyledons, zygotic embryos, meristems and ovum as the target issue can eliminate the need for extensive tissue culture work. Generally, cells derived from meristematic tissue are useful. The method of transformation of meristematic cells of cereal is taught in the PCT application WO96/04392. Any number of various cell lines, tissues, calli and plant parts can and have been transformed by those having knowledge in the art. Methods of preparing callus or protoplasts from various plants are well known in the art and specific methods are detailed in patents and references used by those skilled in the art. Cultures can be initiated from most of the above-identified tissue. The only true requirement of the transforming plant material is that it can ultimately be used to form a transformed plant.

Heterologous means of different natural origin or represents a non-natural state. A host cell transformed with a nucleotide sequence derived from another organism, particularly from another species, that nucleotide sequence is heterologous with respect to that host cell and descendants. Heterologous refers to a nucleotide sequence derived from and inserted into the same natural, original cell type, but which is present in a non-natural state, e.g. a different copy number, or under the control of different regulatory sequences. A transforming nucleotide sequence may comprise a heterologous coding sequence, or heterologous regulatory sequences. Alternatively, the transforming nucleotide sequence may be completely heterologous or may comprise any possible combination of heterologous and endogenous nucleic acid sequences.

The DNA used for transformation of these plants clearly may be circular, linear, and double or single stranded. The DNA is placed within a plasmid. The plasmid usually contains regulatory and/or targeting sequences which assists the expression or targeting of the gene in the plant. The methods of forming plasmids for transformation are known in the art. Plasmid components can include such items as: leader sequences, transit polypeptides, promoters, terminators, genes, introns, marker genes, etc. The gene orientations can be sense, antisense, partial antisense or partial sense; and, multiple gene copies can be used. The transgene can come from plants or be from various non-plant genes such as; bacteria, yeast, animals, and viruses.

The regulatory promoters employed can be constitutive such as CaMv35S (usually for dicots) and polyubiquitin for monocots or tissue specific promoters such as CAB promoters, MR7 described in U.S. Pat. No. 5,837,848, etc. The prior art promoters, includes but is not limited to, octopine synthase, nopaline synthase, CaMv19S, mannopine synthase. These regulatory sequences can be combined with introns, terminators, enhancers, leader sequences and the like in the material used for transformation.

The isolated DNA is then transformed into the plant. A transgene introgressed into this invention typically comprises a nucleotide sequence whose expression is responsible or contributes to the trait under the control of a promoter appropriate for the expression of the nucleotide sequence at the desired time in the desired tissue or part of the plant. Constitutive or inducible promoters are used. The transgene may also comprise other regulatory elements, such as, for example translation enhancers or termination signals. In an embodiment, the nucleotide sequence is the coding sequence of a gene and is transcribed and translated into a protein. In another embodiment, the nucleotide sequence encodes an antisense RNA, a sense RNA that is not translated or only partially translated, a t-RNA, a r-RNA or a sn-RNA.

The genes responsible for a specific gene trait are generally inherited through the nucleus. Known exceptions are, e.g. the genes for male sterility, some of which are inherited cytoplasmically, but still act as single gene traits. In one embodiment, a heterologous transgene to be transferred to present invention is integrated into the nuclear genome of the donor, non-recurrent parent. In another embodiment, a heterologous transgene to be transferred into the present invention is integrated into the plastid genome of the donor, non-recurrent parent.

In an embodiment, a transgene whose expression results or contributes to a desired trait to be transferred to the present invention comprises a virus resistance trait such as, for example, a MDMV strain B coat protein gene whose expression confers resistance to mixed infections of maize dwarf Mosaic virus and maize Chlorotic Mottle virus in transgenic maize plants (Murry et al. Biotechnology (1993) 11:1559 64). In another embodiment, a transgene introgressed into the present invention comprises a gene encoding an insecticidal protein, such as, for example, a crystal protein of *Bacillus thuringiensis* or a vegetative insecticidal protein from *Bacillus cereus*, such as VIP3 (see for example Estruch et al. Nat Biotechnol (1997) 15:137 41. Also see, U.S. Pat. Nos. 5,877,012, 6,291,156; 6,107,279, 6,291,156 and 6,429,360. In another embodiment, an insecticidal gene introduced into present invention is a Cry1Ab gene or a portion thereof, for example introgressed into present invention from a maize line comprising a Bt-11 event as described in U.S. Pat. No. 6,114,608, which is incorporated herein by reference, or from a maize line comprising a 176 event as described in Koziel et al. (1993) Biotechnology 11: 194 200. In yet another embodiment, a transgene introgressed into present invention comprises a herbicide tolerance gene. For example, expression of an altered acetohydroxyacid synthase (AHAS) enzyme confers upon plants tolerance to various imidazolinone or sulfonamide herbicides (U.S. Pat. No. 4,761,373). In another embodiment, a non-transgenic trait conferring tolerance to imidazolinones is introgressed into present invention (e.g. a "IT" or "IR" trait). U.S. Pat. No. 4,975,374, incorporated herein by reference, relates to plant cells and plants containing a gene encoding a mutant glutamine synthetase (GS) resistant to inhibition by herbicides that are known to inhibit GS, e.g. phosphinothricin and methionine sulfoximine. Also, expression of a *Streptomyces* bar gene encoding a phosphinothricin acetyl transferase in maize plants results in tolerance to the herbicide phosphinothricin or glufosinate (U.S. Pat. No. 5,489,520). U.S. Pat. No. 5,013,659, which is incorporated herein by reference, is directed to plants that express a mutant acetolactate synthase (ALS) that renders the plants resistant to inhibition by sulfonylurea herbicides. U.S. Pat. No. 5,162,602 discloses plants tolerant to inhibition by cyclohexanedione and aryloxyphenoxypropanoic acid herbicides. The tolerance is conferred by an altered-acetyl coenzyme A carboxylase (ACCase). U.S. Pat. No. 5,554,798 discloses transgenic glyphosate tolerant maize plants, which tolerance is conferred by an altered 5-enolpyruvyl-3-phosphoshikimate (EPSP) synthase gene. U.S. Pat. No. 5,804,425 discloses transgenic glyphosate tolerant maize plants, which tolerance is conferred by an EPSP synthase gene derived from *Agrobacterium tumefaciens* CP-4 strain. Also, tolerance to a protoporphyrinogen oxidase inhibitor is achieved by expression of a tolerant protoporphyrinogen oxidase enzyme in plants (U.S. Pat. No. 5,767,373). Another trait transferable to the present invention confers a safening effect or additional tolerance to an inhibitor of the enzyme hydroxyphenylpyruvate dioxygenase (HPPD) and transgenes conferring such trait are, for example, described in WO 9638567, WO 9802562, WO 9923886, WO 9925842, WO 9749816, WO 9804685 and WO 9904021. All issued patents referred to herein are, in their entirety, expressly incorporated herein by reference.

In an embodiment, a transgene transferred to present invention comprises a gene conferring tolerance to a herbicide and at least another nucleotide sequence encoding another trait, such as for example, an insecticidal protein. Such combination of single gene traits is for example a Cry1Ab gene and a bar gene.

By way of example only, specific events (followed by their APHIS petition numbers) that can be transformed or introgressed into maize plants include the glyphosate tolerant event GA21 (97-09901p) or the glyphosate tolerant event NK603 (00-011-01p), the glyphosate tolerant/Lepidopteran insect resistant event MON 802 (96-31701p) Mon810, Lepidopteran insect resistant event DBT418 (96-29101p), male sterile event MS3 (95-22801p), Lepidopteran insect resistant event Bt11 (95-19501p), phosphinothricin tolerant event B16 (95-14501p), Lepidopteran insect resistant event MON 80100 (95-09301p) and MON 863 (01-137-01p), phosphinothricin tolerant events T14, T25 (94-35701p), Lepidopteran insect resistant event 176 (94-31901p) and Western corn rootworm (04-362-01p), and the phosphinothricin tolerant and Lepidopteran insect resistant event CBH-351 (92-265-01p).

After the transformation of the plant material is complete, the next step is identifying the cells or material, which has been transformed. In some cases, a screenable marker is employed such as the beta-glucuronidase gene of the uidA locus of *E. coli*. Then, the transformed cells expressing the colored protein are selected. In many cases, a selectable marker identifies the transformed material. The putatively transformed material is exposed to a toxic agent at varying concentrations. The cells not transformed with the selectable marker, which provides resistance to this toxic agent, die.

Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. If the transformed material was cell lines then these lines are regenerated into plants. The cells' lines are treated to induce tissue differentiation. Methods of regeneration of cellular maize material are well known in the art.

As used herein, the term "plant" includes plant cells, plant protoplasts, plant cell tissue cultures from which maize plants can be regenerated, plant calli, plant clumps, and plant cells that are intact in plants or parts of plants, such as embryos, pollen, ovules, flowers, kernels, ears, cobs, leaves, husks, stalks, roots, root tips, anthers, silk, seeds and the like.

Duncan, Williams, Zehr, and Widholm, Planta (1985) 165: 322 332 reflects that 97% of the plants cultured that produced callus were capable of plant regeneration. Subsequent experiments with both inbreds and hybrids produced 91% regenerable callus that produced plants. In a further study in 1988, Songstad, Duncan & Widholm in Plant Cell Reports (1988), 7:262 265 reports several media additions that enhance regenerability of callus of two inbred lines. Other published reports also indicated that "nontraditional" tissues are capable of producing somatic embryogenesis and plant regeneration. K. P. Rao, et al., Maize Genetics Cooperation Newsletter, 60:64 65 (1986), refers to somatic embryogenesis from glume callus cultures and B. V. Conger, et al., Plant Cell Reports, 6:345 347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture procedures of maize are described in Green and Rhodes, "Plant Regeneration in Tissue Culture of Maize,"

Maize for Biological Research (Plant Molecular Biology Association, Charlottesville, Va. 1982, at 367 372) and in Duncan, et al., "The Production of Callus Capable of Plant Regeneration from Immature Embryos of Numerous *Zea mays* Genotypes," 165 Planta 322 332 (1985). Thus, another aspect of this invention is to provide cells that upon growth and differentiation produce maize plants having the physiological and morphological characteristics of the present invention. In an embodiment of the invention, cells of the present invention are transformed genetically, for example with one or more genes described above, by using a transformation method described in U.S. Pat. No. 6,114,608, wherein transgenic plants of the present invention are obtained and used for the production of hybrid maize plants.

The introgression of a Bt11 event into a maize line, such as present invention, by backcrossing is exemplified in U.S. Pat. No. 6,114,608, and the present invention is directed to methods of introgressing a Bt11 event into present invention and to progeny thereof using, for example, the markers described in U.S. Pat. No. 6,114,608.

Direct selection may be applied where the trait acts as a dominant trait. An example of a dominant trait is herbicide tolerance. For this selection process, the progeny of the initial cross are sprayed with the herbicide prior to the backcrossing. The spraying eliminates any plant that does not have the desired herbicide tolerance characteristic, and only those plants that have the herbicide tolerance gene are used in the subsequent backcross. This process is then repeated for the additional backcross generations.

Maize is used as food, feed, and in industry. Sweet corn is canned and frozen for human consumption. Maize, food products such as grits, meal, flour, starch, maize syrups, and dextrose also come from the dry- and wet-milling industries. Maize oil from maize germ is also a by-product of the milling industries.

Maize is a primary livestock feed for cattle, hogs, and poultry. Industrial use of maize includes production of ethanol, starch or pastes. The industrial applications of maize paste require specific viscosity, adhesiveness, and suspension characteristics. The paste and flour are used in paper and textiles.

The seed of the present invention or of the present invention further comprising one or more single gene traits, the plant produced from the inbred seed, the hybrid maize plant produced from the crossing of the inbred, hybrid seed, and various parts of the hybrid maize plant can be utilized for human food, livestock feed, and as a raw material in industry.

The present invention therefore also discloses an agricultural product comprising a plant of the present invention or derived from a plant of the present invention. The present invention also discloses an industrial product comprising a plant of the present invention or derived from a plant of the present invention. The present invention further discloses methods of producing an agricultural or industrial product comprising planting seeds of the present invention, growing plant from such seeds, harvesting the plants and processing them to obtain an agricultural or industrial product.

A deposit of at least 2500 seeds of this invention will be maintained by Syngenta Seed Inc. Access to this deposit will be available during the pendency of this application to the Commissioner of Patents and Trademarks and persons determined by the Commissioner to be entitled thereto upon request. All restrictions on availability to the public of such material will be removed upon issuance of a granted patent of this application by depositing at least 2500 seeds of this invention at the American Type Culture Collection (ATCC), at 10801 University Boulevard, Manassas, Va. 20110. The ATCC number of the deposit is PTA-10377. The date of deposit was Oct. 1, 2009 and the seed was tested on Oct. 13, 2009 and found to be viable. The deposit of at least 2500 seeds will be from inbred seed taken from the deposit maintained by Syngenta Seed Inc. The ATCC deposit will be maintained in that depository, which is a public depository, for a period of 30 years, or 5 years after the last request, or for the enforceable life of the patent, whichever is longer, and will be replaced if it becomes nonviable during that period.

Additional public information on patent variety protection may be available from the PVP Office, a division of the U.S. Government.

Accordingly, the present invention has been described with some degree of particularity directed to the embodiment of the present invention. It should be appreciated, though that the present invention is defined by the following claims construed in light of the prior art so that modifications or changes may be made to the embodiment of the present invention without departing from the inventive concepts contained herein.

I claim:

1. A seed of the maize inbred line G07-NPID4480, representative seed of said line having been deposited under ATCC Accession Number PTA-10377.

2. A maize plant or plant part produced by growing the seed of claim 1.

3. An F1 hybrid maize seed produced by crossing a plant of maize inbred line G07-NPID4480 according to claim 2 with a different maize plant and harvesting the resultant F1 hybrid maize seed.

4. A maize plant or plant part produced by growing the F1 hybrid maize seed of claim 3.

5. An F1 hybrid maize seed comprising an inbred maize plant cell of inbred maize line G07-NPID4480, representative seed of said line having been deposited under ATCC Accession Number PTA-10377.

6. A maize plant produced by growing the F1 hybrid maize seed of claim 5.

7. A cell of a maize plant produced by growing the F1 hybrid maize seed of claim 5.

8. A process of introducing a desired trait into maize inbred line G07-NPID4480 comprising: (a) crossing G07-NPID4480 plants grown from G07-NPID4480 seed, representative seed of which has been deposited under ATCC Accession Number PTA-10377, with plants of another maize line that comprise a desired trait to produce F1 progeny plants, wherein the desired trait is selected from the group consisting of waxy starch, male sterility, herbicide resistance, insect resistance, bacterial disease resistance, fungal disease resistance, and viral disease resistance; (b) selecting F1 progeny plants that have the desired trait to produce selected F1 progeny plants; (c) crossing the selected progeny plants with the G07-NPID4480 plants to produce backcross progeny plants; (d) selecting for backcross progeny plants that have the desired trait to produce selected backcross progeny plants; and (e) repeating steps (c) and (d) at least three or more times to produce backcross progeny plants that comprise the desired trait and all of the physiological and morphological characteristics of corn inbred line G07-NPID4480 listed in Table 1 when grown in the same environmental conditions.

9. A plant produced by the process of claim 8.

10. A maize plant having all the physiological and morphological characteristics of inbred line G07-NPID4480, wherein a sample of the seed of inbred line G07-NPID4480 was deposited under ATCC Accession Number PTA-10377.

11. A process of producing maize seed, comprising crossing a first parent maize plant with a second parent maize plant, wherein one or both of the first or the second parent maize plants is the plant of claim 10, and harvesting the resultant seed.

12. The maize seed produced by the process of claim 11.

13. The maize seed of claim 12, wherein the maize seed is hybrid seed.

14. A hybrid maize plant, or its parts, produced by growing said hybrid seed of claim 13.

15. The maize plant of claim 10, further comprising a genome comprising at least one transgene or a gene conversion conferred by a transgene.

16. The maize plant of claim 15, wherein the gene confers a trait selected from the group consisting of herbicide tolerance; insect tolerance; resistance to bacterial, fungal, nematode or viral disease; waxy starch; male sterility or restoration of male fertility, modified carbohydrate metabolism and modified fatty acid metabolism.

17. A method of producing a maize plant derived from the inbred line G07-NPID4480, the method comprising the steps of (a) growing a progeny plant produced by crossing the plant of claim 10 with a second maize plant; (b) crossing the progeny plant with itself or a different plant to produce a seed of a progeny plant of a subsequent generation; (c) growing a progeny plant of a subsequent generation from said seed and crossing the progeny plant of a subsequent generation with itself or a different plant; and (d) repeating steps (b) and (c) for an additional 0-5 generations to produce a maize plant derived from the inbred line G07-NPID4480.

18. A method for developing a maize plant in a maize plant breeding program, comprising applying plant breeding techniques to the maize plant of claim 10, or its parts, wherein application of said techniques results in development of a maize plant.

19. The method for developing a maize plant in a maize plant breeding program of claim 18, wherein the plant breeding techniques are selected from the group consisting of recurrent selection, backcrossing, pedigree breeding, restriction fragment length polymorphism enhanced selection, genetic marker enhanced selection, and transformation.

* * * * *